United States Patent [19]
Hirth et al.

[11] Patent Number: 5,763,198
[45] Date of Patent: Jun. 9, 1998

[54] SCREENING ASSAYS FOR COMPOUNDS

[75] Inventors: Klaus Peter Hirth; Harald App; Jianming Tsai, all of San Francisco, Calif.

[73] Assignee: Sugen, Inc., Redwood City, Calif.

[21] Appl. No.: 279,321

[22] Filed: Jul. 22, 1994

[51] Int. Cl.$^6$ .................................................. G01N 33/543
[52] U.S. Cl. ...................... 435/7.21; 435/7.23; 435/7.24; 435/7.94; 435/15; 435/21; 435/29; 436/518; 436/548
[58] Field of Search ................................ 435/7.21, 7.23, 435/7.24, 7.4, 7.94, 15, 21, 29; 436/518, 548

[56] References Cited

U.S. PATENT DOCUMENTS

| | | | |
|---|---|---|---|
| 4,215,051 | 7/1980 | Schroeder et al. | 260/346.7 |
| 4,478,946 | 10/1984 | Van der Merwe et al. | 436/518 |
| 4,946,778 | 8/1990 | Ladner et al. | 435/69.6 |
| 5,427,916 | 6/1995 | Gerwitz et al. | 436/813 |
| 5,527,688 | 6/1996 | Millia | 435/15 |
| 5,538,858 | 7/1996 | Mallia | 435/15 |
| 5,580,742 | 12/1996 | Bodenmuller et al. | 435/7.94 |
| 5,599,681 | 2/1997 | Epstein et al. | 435/7.23 |

FOREIGN PATENT DOCUMENTS

| | | |
|---|---|---|
| WO 90/10234 | 9/1990 | WIPO . |
| WO 93/21230 | 10/1993 | WIPO . |

OTHER PUBLICATIONS

Millauer et al., 1994. "Glioblastoma Growth Inhibited in vivo by a Dominant–Negative Flk–1 Mutant," Nature 367:576–579.

Fu et al., 1993. "Transcription Factor p91 Interacts with the Epidermal Growth Factor Receptor and Mediates Activation of the c–fos Gene Promoter," Cell 74:1135–1145.

Musacchio et al., 1993. "The PH Domain: a Common Piece in the Structural Patchwork of Signalling Proteins," TBIS 18:343–348.

Katagiri et al., 1993. "Tyrosine–Phosphorylation of Tubulin during Nonocytic Differentiation of HL–60 Cells," J. Immunol. 150:585–593.

Schraag et al., 1993. "Standardization of an Enzyme–Linked Immunosorbent Assay for the Determination of Protein Tyrosine Kinase Activity," Analytical Biochem. 211:233–239.

Walton et al., 1993. "Protein Tyrosine Phosphatases." Annu. Rev. Biochem. 62:101–20.

Pawson et al., 1993. "SH2 and SH3 Domains," Current Biology 3:434–442.

Hansen et al., 1993. "Application of Two–Dimensional Gel Analysis to Identification and Characterization of Tyrosine Phosphorylated Substrates for Growth Factors Receptors," Electrophoresis 14:112–126.

Campbell et al., 1993. "Evidence for Involvement of the Growth Hormone Receptor–Associated Tyrosine Kinase in Actions of Growth Hormone," J. Biol. Chem. 268:7427–7434.

Pawson et al., 1992. "SH2 and SH3 Domains: From Structure to Function," Cell 71:359–362.

Schlessinger et al., 1992. "Growth Factor Signalling by Receptor Tyrosine Kinases," Neuron 9:383–391.

Pelicci et al., 1992. "A Novel Transforming Protein (SHC) with an SH2 Domain is Implicated in Mitogenic Signal Transduction," Cell 70:93–104.

Farley et al., 1992. "Development of Solid–Phase Enzyme–Linked Immunosorbent Assays for the Determination of Epidermal Growth Factor Receptor and pp60$^{c-src}$ Tyrosine Protein Kinase Activity," Analytical Biochem. 203:151–157.

Peraldi et al., 1992. "Dephosphorylation of Human Insulin–Like Growth Factor I (IGF–I) Receptors by Membrane–Associated Tyrosine Phosphatases," Biochem J. 285:71–78.

Koch et al., 1991. "SH2 and SH3 Domains: Elements That Control Interactions of Cytoplasmic Signaling Proteins," Science 252:668–674.

Donato et al., 1991. "Tumor Necrosis Factor Regulates Tyrosine Phosphorylation on Epidermal Growth Factor Receptors in A431 Carcinoma Cells: Evidence for a Distinct Mechanism," Cell Growth & Differentiation 3:259–268.

Aaronson et al., 1991. "Growth Factors and Cancer," Science 254:1146–1153.

Ueno et al., 1991. "Inhibition of PDGF $\beta$ Receptor Signal Transduction by Coexpression of a Truncated Receptor," Science 252:844–848.

Skolinik et al., 1991. "Cloning of P13 Kinase–Associated p85 Utilizing a Novel Method for Expression/Cloning of Target Proteins for Receptor Tyrosine Kinases," Cell 65:83–90.

Cantley et al., 1991. "Oncogenes and Signal Transduction," Cell 64:281–302.

Lazaro et al., 1991. "Description of an Enzyme–Linked Immunosorbent Assay for the Detection of Protein Tyrosine Kinase," Analytical Biochem. 192:257–261.

Tonks et al., 1991. "Purification of Protein–Tyrosine Phosphatases from Human Placenta," Methods in Enzymology 201:427–442.

(List continued on next page.)

*Primary Examiner*—David Saunders
*Attorney, Agent, or Firm*—Pennie & Edmonds LLP

[57] ABSTRACT

The invention is directed to rapid and quantitative assay systems for screening test compounds for their ability to modulate tyrosine kinase or phosphatase activities involved in signal transduction by determining the tyrosine phosphorylation state of a protein substrate using an anti-phosphotyrosine antibody and an antibody specific for the protein substrate. These assays may be practiced in a whole cell or cell-free system. The assays can be used to identify test compounds for use in therapeutic applications to disease processes in which tyrosine kinase or phosphatase activity in a signal transduction pathway contributes to a pathological process.

22 Claims, No Drawings

OTHER PUBLICATIONS

Bjorge et al., 1990, "Activated Type 1 Phosphatidylinositol Kinase is Associated with the Epidermal Growth Factor (EGF) Receptor Following EGF Stimulation," Biochemistry 87:3816–3820.

Ullrich et al., 1990, "Signal Transduction by Receptors with Tyrosine Kinases Activity," Cell 61:203–212.

Fendly et al., 1990, "Characterization of Murine Monoclonal Antibodies Reactive to Either the Human Epidermal Growth Factor Receptor or HER2/neu Gene Product," Cancer Research 50:1550–1558.

Cleaveland et al., "A Microtiter-Based Assay for the Detection of Protein Tyrosine Kinase Activity," Analytical Biochem. 190:249–253.

Rijksen et al., 1989, "A Nonradioactive Dot–Blot Assay for Protein Kinase Activity," Analytical Biochem. 182:98–102.

Huse et al., "Generation of a Large Combination Library of the Immunoglobulin Repertoire in Phage Lambda," Science 246:1275–1281.

Margolis et al., 1989, "EGF Induces Tyrosine Phosphorylation of Phospholipase C–II: A Potential Mechanism for EGF Receptor Signalling," Cell 57:1101–1107.

Van Heede et al., 1989, "Expression of Human Asparagine Synthetase in *Escherichia coli*," J. Biol. Chem. 264:5503–5509.

Drebin et al., 1989, "Monoclonal Antibodies Specific for the neu Oncogene Product Directly Mediate Anti–Tumor Effects in vivo," Oncogene 2:387–394.

Schlessinger, J., 1988, "Signal Transduction by Allosteric Receptor Oligomerization," TIBS 13:443–447.

Harlow & Lane ed., 1988, "Storing and Purifying Antibodies," (in *Antibodies: A Laboratory Manual*, Cold Springs Harbor Laboratory Press) 283–318.

Honegger et al., 1987, "Point Mutation at the ATP Binding Site of EGF Receptor Abolishes Protein–Tyrosine Kinase Activity and Alters Cellular Routing," Cell 51:199–209.

Slamon et al., 1987, "Human Breast Cancer: Correlation of Relapse and Survival with Amplification of the HER–2/neu Oncogene," Science 235:177–182.

Bitter et al., 1987, "Expression and Secretion Vectors for Yeast," Methods in Enzymology 153:516–544.

Takeda et al., 1985, "Construction of Chimaeric Processed Immunoglobulin Genes Containing Mouse Variable and Human Constant Region Sequences," Nature 314:452–454.

Cole et al., 1985, "The EBV–Hybridoma Technique and Its Application to Human Lung Cancer," (in *Monoclonal Antibodies and Cancer Therapy*, Albert R. Liss Inc.) 77–96.

Inouye et al., 1985, "Up–Promoter Mutations in the Ipp Gene of *Escherichia coli*," Nucleic Acids Research 13:3101–3110.

Neuberger et al., 1984, "Recombinant Antibodies Possessing Novel Effector Functions," Nature 312:604–608.

Morrison et al., 1984, "Chimeric Human Antibody Molecules: Mouse Antigen–Binding Domains with Human Constant Region Domains," Proc. Natl. Acad. Sci. USA 81:6851–6855.

Logan et al., 1984, "Adenovirus Tripartite Leader Sequence Enhances Translation of mRNA Late After Infection," Proc. Natl. Acad. Sci. USA 81:3655–3659.

Smith et al., 1983, "Molecular Engineering of the *Autographa Californica* Nuclear Polyhedrosis Virus Genome: Deletion Mutations Within the Polyhedrin Gene," J. Virology 46:584–593.

Cote et al., 1983, "Generation of Human Monoclonal Antibodies Reactive with Cellular Antigens," Proc. Natl. Acad. Sci. USA 80:2026–2030.

Ruther et al., 1983, "Easy Identification of cDNA Clones," EMBO 2:1791–1794.

Kozbor et al., 1983, "The Production of Monoclonal Antibodies from Human Lymphocytes," Immunol. Today 4:72–79.

Tsang et al., 1983, "Enzyme–Linked Immunoelectrotransfer Blot Techniques (EITB) for Studying the Specificities of Antigens and Antibodies Separated by Gel Electorphoresis," Methods in Enzymology 92:377–391.

Kohler et al., 1975, "Continuous Cultures of Fused Cells Secreting Antibody of Predefined Specificity," Nature 256:495–497.

Gazit et al., 1991, "Tyrphostins. 2. Heterocyclic and α–substituted benzylidenemalonitrile tyrphostins as potent inhibitors of EGF receptor and ErbB2/neu tyrosine kinases", J Med Chem 34:1896–1907.

Ohmichi et al., 1993, "The tyrosine kinase inhibitor tyrphostin blocks the cellular actions of nerve growth factor", Biochemistry 32:4650–4658.

Creighton, 1984, in *Proteins: Structure and Molecular Principles*, W.H. Freeman and Co., NY, pp. 55–60.

Harlow & Lane ed., 1988, "Labeling Antibodies", in *Antibodies: A Laboratory Manual*, Cold Spring Harbor Laboratory Press, Chapter 9, pp. 319–358.

King et al., 1993, "High throughput assay inhibitors of the epidermal growth factor receptor–associated tyrosine kinase", Life Sciences 53:1465–1472.

V. P. Knutson et al, Arch. Biochem. Biophys., 285, 197–204, 1991.

P. Tijssen, Practice and Theory of Enzyme Immunoassays, Elsevier Science Publishers B.V., 1985, pp. 329–343.

SCREENING ASSAYS FOR COMPOUNDS

1. INTRODUCTION

The invention relates to rapid, quantitative, specific, high through-put assay systems for screening test compounds for their ability to modulate tyrosine kinase or phosphatase activity within the cell or in a cell-free system.

2. BACKGROUND OF THE INVENTION

Protein phosphorylation is a common regulatory mechanism used by cells to selectively modify proteins carrying regulatory signals from outside the cell to the nucleus. The proteins that execute these biochemical modifications are a group of enzymes known as protein kinases. They may further be defined by the substrate residue that they target for phosphorylation. One group of protein kinases are the tyrosine kinases (TKs) which selectively phosphorylate a target protein on its tyrosine residues. Some tyrosine kinases are membrane-bound receptors (RTKs), and, upon activation by a ligand, can autophosphorylate as well as modify substrates. The initiation of sequential phosphorylation by ligand stimulation is a paradigm that underlies the action of such effectors as, for example, epidermal growth factor (EGF), insulin, platelet-derived growth factor (PDGF), and fibroblast growth factor (FGF). The receptors for these ligands are tyrosine kinases and provide the interface between the binding of a ligand (hormone, growth factor) to a target cell and the transmission of a signal into the cell by the activation of one or more biochemical pathways. Ligand binding to a receptor tyrosine kinase activates its intrinsic enzymatic activity. (Ullrich and Schlessinger, Cell 61:203–212, 1990). Tyrosine kinases can also be cytoplasmic, non-receptor-type enzymes and act as a downstream component of a signal transduction pathway.

The cell has evolved a class of enzymes that complement protein kinases, known as protein phosphatases, which remove the added phosphates. Phosphotyrosine phosphatases (PTPs), specifically remove the phosphates from tyrosine residues of modified proteins, although some may also have enzymatic activity for other phosphoamino acids. As with the TKs, these phosphatases may be transmembrane molecules or they may be localized in intracellular compartments (Walton et al., 1993, Ann. Rev. Biochem. 62:101–120). These proteins also play an integral role in the signal transduction pathways of the cell.

The secondary signal transduction molecules generated by activated receptors result in a signal cascade that regulates cell functions such as cell division, differentiation and survival. These molecules can be cytoplasmic enzymes such as, for example, kinases and phosphatases or can be non-catalytic adapter molecules such as, for example, the Grbs (Growth factor Receptor Bound) (Skolnik, et al., 1991, Cell 65:83–90). Adapter proteins have in common one or two copies of an approximately 100 amino acid long motif called an SH2 (Src homology 2) domain due to its similarity to a motif originally identified in the c-Src cytoplasmic TKs. SH2-containing polypeptides may otherwise be structurally and functionally distinct from one another (Koch, C. A. et al. 1991, Science 252:66–674). SH2 domains directly recognize specific phosphorylated tyrosine residues. There is evidence that the amino acid sequences flanking the phosphorylated tyrosine confers a certain specificity such that a particular SH2 domain will bind preferentially to particular sequences (Koch. C. A., et al. 1991, Science 252:668–674; Cantley, L. C., et al. 1991, Cell 64:281–302).

In addition to SH2 domains, many of the adapter proteins involved in signal transduction contain a conserved motif of 50–75 amino acids know as an SH3 (Src-homology 3) domain (see for example, Schlessinger & Ullrich, 1992, Neuron 9:383–391). In the case of SH3 domains, it is known that proteins with SH3 domains bind to proteins with proline rich regions, such as, for example, —PPPLPP—. A third domain known as the pleckstrin-homology or PH domain, has also been identified in many adapter type proteins (Musacchio et al., 1993, TIBS 18:342–348). Much less is known about the biological role of these domains; however, it is believed that they are involved in protein-protein interactions between components of signal transduction pathways (Pawson & Gish, 1992, Cell 71:359–362; Pawsom & Schlessinger, 1993, Current Biology 3:424–442). Reviews describing intracellular signal transduction include Aaronson, S. A., 1991, Science 254:1146–1153; Schlessinger, J., 1988, Trends Biochem. Sci. 13:443–447; and Ullrich & Schlessinger, 1990, Cell 61:203–212.

The profound cellular effects mediated by tyrosine kinases and phosphotyrosine phosphatases have made them attractive targets for the development of new therapeutic molecules. It is known, for example, that the overexpression of tyrosine kinases, such as HER2, can play a decisive role in the development of cancer (Slamon, D. J., et al., 1987, Science, 235:177–182) and that antibodies capable of blocking the activity of this enzyme can abrogate tumor growth. (Drebin, et al. 1988, Oncogene 2:387–394). Blocking the signal transduction capability of tyrosine kinases such as Flk-1 and the PDGF receptor have been shown to block tumor growth in animal models (Millauer, B., et al. 1994, Nature 367:577; Ueno, H., et al. 1991, Science 252:844–848).

Assays currently used for screening drugs/ligands that act on cells containing TKs, in general, involve exposing cells that express the TK to a test substance and either: (a) scoring phenotypic changes in the cell culture as compared to control cells that were not exposed to the test substance; or (b) biochemically analyzing cell lysates to assess the level and/or identity of tyrosine phosphorylated proteins.

This latter approach is illustrated by several methodologies. A common technique involves incubating cells with ligand and radiolabeled phosphate, lysing the cells, separating cellular protein components of the lysate using an SDS-polyacrylamide gel (SDS-PAGE) technique, in either one or two dimensions, and detecting the presence of phosphorylated proteins by exposing X-ray film. In a similar technique, the phosphorylated proteins are detected by immunoblotting techniques, in which case the phosphate that is detected is not radiolabeled. Instead, the cellular components separated by SDS-PAGE are transferred to a nitrocellulose membrane, where the presence of phosphorylated tyrosines is detected using an antiphosphotyrosine antibody (anti-PY). The anti-PY can be detected by labeling it with a radioactive substance, which then requires scanning the labeled nitrocellulose with a piece of specialized equipment designed to detect radioactivity or exposure of X-ray film. Alternatively, the anti-PY can be conjugated with an enzyme, such as horseradish peroxidase, and detected by subsequent addition of a colorometric substrate for the enzyme. A further alternative involves detecting the anti-PY by reacting with a second antibody which recognizes the anti-PY, this second antibody being labeled with either a radioactive moiety or an enzyme as previously described. Examples of these and similar techniques are described in Hansen et al., 1993, Electrophoresis 14:112–126; Campbell et al. 1993, J. Biol. Chem. 268:7427–7434; Donato et al., 1992, Cell Growth and Diff. 3:258–268; and Katagiri et al., 1993, J. Immunol. 150:585–593. These techniques have a number of drawbacks that make them unsuitable for rapid screening of a large number of test substances including the undesirable use of radioactive substances, the lack of specificity for particular cellular components of interest due to the use of total cellular lysate, the relatively large amount of handling required to process each sample, and the limited number of samples that can be accommodated by gel electrophoresis.

ELISA-type assays in microtitre plates have been used to test purified substrates. See for example Peraldi et al., 1992, J. Biochem. 285: 71–78; Schraag et al., 1993, Analytical Biochemistry 211:233–239; Cleavland, 1990, Analytical Biochemistry 190:249–253; Farley, 1992, Analytical Biochemistry 203:151–157; and Lczaro, 1991, Analytical Biochemistry 192:257–261. However, these techniques involve assaying purified components, and thus are unsuitable for evaluating the effects of a test substance on phosphorylation within the normal cellular context. Purified components may be difficult or expensive to obtain in sufficient quantities or may require significant experimental work to develop a purification process for the desired component.

Although variations on these techniques have been described, to the Applicants' knowledge, a rapid screening assay which is highly specific, quantifiable and amenable to testing a large number of test substances has not been developed.

3. SUMMARY OF THE INVENTION

The present invention relates to rapid, quantitative, specific, high through-put assays for screening test compounds such as drugs, ligands (natural or synthetic), ligand antagonists, peptides, or small organic molecules, for their ability to modulate kinase or phosphatase activities involved in signal transduction.

In accordance with one embodiment of the invention, a target cell that expresses a particular substrate that is phosphorylated or dephosphorylated on tyrosine residues during signal transduction is used. In some cases, the tyrosine kinase is capable of phosphorylating its own specific tyrosine residues, in which case the kinase enzyme is also the substrate. The target cell is exposed to a test substance, and thereafter lysed to release cellular contents, including the protein substrate. The substrate is isolated by contacting the cell lysate with a substrate-specific antibody immobilized directly or indirectly onto a solid support and subsequently washing away the majority of other cellular components, some of which may also be phosphorylated. An assay is performed on the isolated substrate to detect the presence or absence of phosphotyrosine residues on the substrate compared to lysates of control target cells which were not exposed to the test substance.

Where mimetics of the natural ligand of a signal transducing receptor are to be screened, the target cells are exposed to the test substance in the absence of ligand and the results compared to negative controls that were not exposed to either the ligand or the test substance, and to positive controls that were exposed to ligand only. When inhibitors or enhancers of ligand activity are to be screened, the target cells are exposed to the test compound in the presence of the ligand and results are compared to those of controls where the cells are exposed only to ligand.

In accordance with another embodiment of the invention, the effect of test substances on the ability of the kinases and phosphotyrosine phosphatases to phosphorylate and dephosphorylate, respectively, tyrosine residues of a particular substrate can be tested in a cell free system. To this end, an appropriate reaction mixture is prepared containing the substrate and kinase (these are one and the same in the case when autophosphorylation is measured) or the phosphorylated substrate and phosphatase. The kinase reaction is initiated in the presence of ATP and divalent cations. An immunoassay is performed on the reaction product to detect the presence or absence of phosphotyrosine residues on the substrate, and results are compared to those obtained for controls.

Detection of the presence or absence of phosphotyrosine residues on a target substrate is performed in one of several ways. One method (immunoassay or sandwich ELISA) utilizes a signal-generating anti-phosphotyrosine antibody to detect phosphotyrosine residues on the immobilized substrate thereby measuring the degree of phosphorylation of the substrate. In a second method, detection of the presence or absence of phosphotyrosine is accomplished by the binding of a specific SH2 domain or SH2 domain containing protein. Said SH2 domain or SH2 domain containing protein will be relatively specific for a particular phosphorylated tyrosine. SH2 domain containing proteins are, for example but not limited to, Grb molecules such as Grb2 (Margolis, B., et al. 1989, Cell 51:1101–1107; Bjoige, et al. 1990, Proc. Nat. Acad. Sci. USA 87:3816–3820; Pelicci, et al. 1992, Cell 70:93–104; Fu & Zhang, 1993, Cell 74:1135–1145). The degree of binding of the SH2 domain or SH2 domain containing protein can be accomplished with a signal-generating anti-SH2 domain or anti-SH2 domain containing protein antibody or by, for example, using an SH2 domain or SH2 domain containing protein fused to a signal-generating protein, such as, for example GST (glutathione-s-transferase, Tsang, V. C. W., et al. Methods in Enzymology 92:377, 1983).

The invention is demonstrated by way of working examples using a whole cell assay to screen for inhibitors of EGF-receptor and HER-2 (Section 6, infra); a cell-free assay to screen for inhibitors of the EGF-receptor (Section 7, infra), and a cell-free assay to screen for inhibitors of phosphatase 1B (Section 8, infra).

4. DEFINITIONS

The following terms whether used in the singular or plural shall have the meanings indicated:

Target Cell: a cell which expresses a tyrosine kinase or phosphotyrosine phosphatase of interest, and which further contains a substrate which can be phosphorylated or dephosphorylated as a result of signal transduction. The tyrosine kinase or phosphatase may be naturally expressed by the target cell or engineered into the target cell using recombinant DNA techniques well known in the art.

Test Substance: a chemically defined compound or mixture of compounds (as in the case of a natural extract or tissue culture supernatant) whose effect on the phosphorylation of/by the tyrosine kinases or the dephosphorylation by the tyrosine phosphatases of a target cell is determined by the assay of the invention.

Substrate: a protein which is acted on by tyrosine kinase or tyrosine phosphatases such that it is either phosphorylated or dephosphorylated on tyrosine residues. Tyrosine kinases can act as both a phosphorylating enzyme and a substrate.

Anchoring Molecule: an antibody or other protein which binds specifically to a substrate of a tyrosine kinase or phosphatase and which is immobilized onto a solid phase. The anchoring molecule can be bound directly or indirectly to the solid phase. Indirect binding can be accomplished, for example, by first coating the solid phase with an antibody which binds specifically to the anchoring molecule and subsequently adding the anchoring molecule.

Detection Molecule: an antibody or other protein or amino acid sequence that specifically binds to phosphorylated tyrosine residues, or to a particular phosphorylated tyrosine residue, and which is used in the assay to detect phosphorylated tyrosines on the substrate bound by the anchoring molecule. The detection molecule may be used as an anchoring molecule, in which case the anchoring molecule as defined above is used to detect the level of bound substrate. An example of a protein other than an antibody that specifically binds to phosphorylated tyrosines is a SH2 domain or a protein containing an SH2 domain.

5. DETAILED DESCRIPTION OF THE INVENTION

The present invention relates to methods for screening compounds that modulate kinase or phosphatase activities involved in signal transduction. The assays of the invention involve monitoring the phosphorylation or dephosphorylation of tyrosine residues on selected substrates involved in signal transduction in a target cell and can be practiced in a whole cell or a cell-free system.

Test substances which mimic, enhance or inhibit the signal transduction activity of the natural ligand for the receptor may be readily identified using the assays of the invention. The test substances include but are not limited to hormones that interact with membrane-bound tyrosine kinase receptors, or may be drugs that exert effects on the target cells through the modulation of tyrosine kinases or phosphatases. In this regard, the present invention provides a method for determining the effect of a test substance on specific tyrosine kinases or phosphatases or their substrates in a target cell.

In one embodiment of the invention, target cells that express a protein substrate that is phosphorylated or dephosphorylated on a tyrosine residue during signal transduction are exposed to a test substance and, thereafter, lysed to release cellular contents, including the substrate of interest. Where mimics of the natural ligand for a signal transducing receptor are to be screened, the target cells are exposed to the test substance and compared to positive controls which are exposed only to the natural ligand and to negative controls which were not exposed to either the test substance or the ligand. Where inhibitors or enhancers of ligand-induced signal transduction are to be screened, the target cells are exposed to the natural ligand in the presence of the test substance and compared to controls which are not exposed to the test substance. The substrate of interest is isolated by incubating the cell lysate with a substrate-specific anchoring molecule bound to a solid support and thereafter washing away non-bound cellular components. A detection procedure is performed to assess the presence or absence of phosphotyrosine residues on the substrate as compared to lysates of control cells which were not exposed to the test substance.

This assay offers several advantages. The exposure of the test substance to a whole cell allows for the evaluation of its activity in the natural context in which inhibitors or enhancers of tyrosine kinases may act. As this assay is performed in whole cells and is based on the use of a known phosphorylated substrate, it does not require redesign or the use of reagents specific for the particular kinase or phosphatase responsible for phosphorylating or dephosphorylating said substrate. In addition, radioactive labeling of the target cell proteins is not required in the assay. The assay can detect the effects of the test compounds on cell kinase/phosphatase activities even if the direct target of the compound is unknown. Because this assay, and those described below, can readily be performed in a microtitre plate format, the assays described can be performed by an automated robotic system, allowing for testing of large numbers of test samples within a reasonably short time frame.

The anchoring molecule should be highly specific for the substrate of interest. It is preferred that the anchoring molecule be an antibody, hereinafter referred to as an anchoring antibody. The anchoring antibody is preferably generated against a unique epitope of the substrate, most preferably an epitope wherein binding by the anchoring antibody will not interfere with binding of the detection antibody or SH2 domain. The anchoring antibody may be a monoclonal antibody but can also be a polyclonal antibody.

The detection procedure used to assess the phosphorylation state of the substrate may employ an anti-phosphotyrosine antibody or a peptide that recognizes and binds to phosphorylated tyrosines. Said amino acid sequence may be, for example, an SH2 domain and may furthermore be an isolated SH2 domain or an intact protein containing an SH2 domain. The detection antibody is preferably a polyclonal antibody to maximize the signal but may also be specific monoclonal antibodies which have been optimized for signal generation.

An alternate embodiment of the invention relates to methods for determining the effect of test compounds on the ability of tyrosine kinases to autophosphorylate or phosphorylate the substrate of interest in a cell-free system, or the ability of tyrosine phosphatases to dephosphorylate such substrates in a cell-free system. To assess modulation of enzyme activity, the test substance is added to a reaction mixture containing the kinase or phosphatase and its substrate bound to a solid support by an anchoring antibody. The kinase reaction is initiated by the addition of ATP. A detection procedure as described above is performed on the substrate to assess the presence or absence of the phosphorylated tyrosine residues, and results are compared to those obtained for controls i.e., reaction mixtures to which the test substance was not added.

A further aspect of this embodiment of the invention allows the user to distinguish test substances that inhibit the interaction between the kinase and its substrate from test substances that inhibit the interaction between the kinase and ATP. Test substances that inhibit the interaction between the kinase and its substrate may be more target specific that those that inhibit the interaction between the kinase and ATP.

The assays of the invention can be used as a primary screen to assess the activity of a previously untested compound or extract, in which case a single concentration is tested and compared to controls. This assay can also be used to assess the relative potency of a compound by testing a range of concentrations, in a range of 100 µM to 1 pM, for example, and computing the concentration at which the amount of phosphorylation is reduced by one-half (IC50) compared to controls in the case of inhibitors or increased by one-half relative to the natural ligand in the case of enhancers.

These assays can be used to identify compounds which modulate protein kinase or protein phosphatase activity. It is further contemplated that the assays of the invention can be used to diagnose clinical conditions in which the effect of a known compound on protein kinases or protein phosphatases is altered by reference to a suitable control experiment.

The identification of compounds that modulate protein kinase or protein phosphatase activity can have utility in the selection of compounds to treat neoplastic disorders in which cell proliferation has been shown to correlate with an increase or decrease in kinase or phosphatase activity. For example, in a case where overexpression of a protein kinase, such as HER2, has been shown to correlate with the aberrant growth characteristics of a cell line or tumor, the identification of a compound that can inhibit protein kinase activity may restore normal growth patterns and reverse oncogenicity. In a tumor cell line or tumor in which protein phosphatase activity is decreased, for example, the identification of a compound that stimulates protein phosphatase activity may restore normal growth and reverse oncogenicity.

The compounds identified in the assays of the invention may be used as therapeutic agents against any diseases in which modulation of protein kinase or protein phosphatase activity reverses a pathological process in cells, tissues or organs.

In a further embodiment of the invention, the assays described herein can be used to determine if a cell line or tumor in which aberrant kinase or phosphatase activity contributes to a pathological process or disease state will respond to a compound that modulates kinase or phosphatase activity and therefore reverse the pathological process or disease state. In this manner, therapeutic regimens may be devised using the assays of the invention on cells derived from patients, avoiding the necessity to subject the patient to trial and error.

In addition, if a compound known to modulate kinase or phosphatase activity is shown to cause phenotypic changes in a target-cell, these assays may be used to identify the substrates involved in the signal transduction pathway responsible for the phenotype. Furthermore, the specific kinases or phosphatases operating in the signal pathway that causes a particular phenotype may be identified through an analysis of these substrates.

The whole cell assay of the invention described herein can be performed, for example, by utilizing pre-packaged kits comprising any or all of the reagents of the assay, such as a solid phase coated with an anchoring molecule to a substrate of interest, or a detection molecule. The cell-free assays of the invention may be performed, for example, by utilizing pre-packaged kits comprising any or all of the reagents of the assay, such as an enzyme, substrate, anchoring molecule, a solid phase coated with an anchoring molecule to a substrate of interest, or a detection molecule.

The invention is illustrated in greater detail in the sections that follow and demonstrated by the working examples infra.

5.1. SELECTION OF ASSAY PARAMETERS

Practice of the whole cell assay of the invention requires the selection of an anchoring antibody (or molecule) and a target cell. The anchoring antibody should have a high binding affinity for and be highly specific for the target substrate. The anchoring antibody may be a monoclonal antibody or a polyclonal antibody (see below). Monoclonal antibodies or polyclonal antibodies selective for the substrate are selected by techniques well known in the art. Immunoblots can be performed using lysates from cells that express the target substrate to determine specificity. The preferred antibody will only bind to the substrate, preferably greater than 100,000 molecules per cell. An alternative method for determining specificity is immunoprecipitation. The binding affinity of the monoclonal antibody or polyclonal antibody for the substrate can be determined by the relative strength of the signal generated in the immunoblot or by other techniques well known in the art.

To select a target cell a known number of cells expressing the substrate is lysed and serial dilutions of the lysate are applied to wells in a 96 well microtiter plate that have been precoated with the anchoring antibody. After allowing the substrate to bind to the antibody, the unbound material is washed away and the amount of bound substrate is determined using known immunoassay techniques. In order to have the proper signal to noise ratio one must be able to detect the target molecule in at least $1 \times 10^4$ cell equivalents per well. The maximum number of cells allowable per well is generally $<1 \times 10^5$ due to space constraints although this number may be somewhat larger or smaller depending on the cell type.

The preferred amount of anchoring antibody and the preferred number of cells to be seeded in each well can be determined empirically by varying the amount of anchoring antibody used to coat the well and the amount of cell lysate (whole cell equivalents) added per well. The ideal concentration of these two components will produce a signal which will reflect a specific phosphotyrosine content in a linear part of the curve.

5.2. PREPARATION OF ANTIBODIES USED IN THE ASSAYS

Various procedures known in the art may be used for the production of antibodies to the cellular substrates of interest and/or to the phosphotyrosine residues. Monoclonal or polyclonal antibodies specific for the substrate of interest which may advantageously be used as anchoring antibodies should be prepared against unique epitopes of the substrate to minimize cross reactions with other substrates. Similarly, the detection antibody should only react with a phosphorylated tyrosine amino acid. Monoclonal antibodies or polyclonal antibodies with high binding affinities for such unique epitopes may be used, preferably those that will not interfere with ligand binding if the substrate is also a receptor. For example, where the substrate is a receptor involved in signal transduction, the extracellular domain, which bears unique epitopes that may be involved in ligand recognition and binding, may advantageously be used as the immunogen. For non-receptor substrates where the amino acid sequence is known, non-conserved, variable regions of the protein may be used as immunogens. Anti-phosphotyrosine antibodies may be generated using phosphotyramine epitopes as described in the examples infra. (Fendly et al., 1990, Cancer Research 50:1550–1558)

The antibodies used in the immunoassay include but are not limited to polyclonal, monoclonal, chimeric, single chain, Fab fragments and an Fab expression library. For the production of antibodies, various host animals, including but not limited to rabbits, mice, rats, etc., may be immunized by injection with the particular antigen in a suitable adjuvant or by injecting the epitope conjugated to an immunogenic carrier. Preferably conjugates are prepared so that the most unique epitope of the substrate will be most accessible to antibody. When the substrate of interest is a cell-surface receptor, whole cells expressing said receptor may be used as the antigen. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies may be prepared by using any technique which provides for the production of antibody molecules by continuous cell lines in culture. These include but are not limited to the hybridoma technique originally described by Koehler and Milstein, (Nature, 1975, 256:495–497), the human B-cell hybridoma technique (Kosbor et al., 1983, Immunology Today 4:72) and the EBV-hybridoma technique (Cole et al., 1985, Monoclonal Antibodies and Cancer Therapy, Alan R. Liss, Inc., pp. 77–96). Human antibodies may be used and can be obtained by using human hybridomas (Cote at al., 1983, Proc. Natl. Acad. Sci. 80:2026–2030) or by transforming human B cells with EBV virus in vitro (Cole et al., 1985, in. Monoclonal Antibodies and Cancer Therapy, Alan R. Liss, pp. 77–96). Techniques developed for the production of "chimeric antibodies" (Morrison et al., 1984, Proc. Natl. Acad. Sci. 81:6851–6855; Neuberger et al., 1984, Nature 312:604–608; Takeda et al., 1985, Nature 314:452–454) by splicing the genes from a mouse antibody molecule of appropriate antigen specificity together with genes from a human antibody molecule of appropriate biological activity can be used; such antibodies are within the scope of this invention.

Techniques for the production of single chain antibodies (U.S. Pat. No. 4,946,778) can also be used to produce substrate-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity to antigens.

Antibody fragments which contain binding sites specific for the substrate may be generated by known techniques. For example, such fragments include but are not limited to: the F(ab')2 fragments which can be produced by pepsin digestion of the antibody molecule and the Fab fragments which can be generated by reducing the disulfide bridges of the F(ab')2 fragments.

The antibodies may be stored and purified using methods which are well known to those skilled in the art (e.g., see "Antibodies, A Laboratory-Manual", eds. Harlow & Lane, Cold Spring Harbor Laboratory, 1988, Ch. 8).

Alternatively, polyclonal or monoclonal antibody specific for the substrate of interest may be obtained from commercial sources.

5.3. PREPARATION OF PHOSPHOTYROSINE SPECIFIC PROTEINS USEFUL IN THE ASSAYS

The phosphotyrosine specific proteins or peptides used for the detection procedures are produced by methods well known to those skilled in the art. They may be purified from cells that natively express the protein, or may be produced by recombinant means and purified from genetically engineered cells. A variety of host-expression vector systems may be utilized to express the coding sequences of said protein or peptides. These include but are not limited to microorganisms such as bacteria (e.g., E.coli, B. subtilis) transformed with recombinant bacteriophage DNA, plasmid DNA or cosmid DNA expression vectors containing PTK or adaptor protein coding sequences; yeast (e.g., Saccharomyces, Pichia) transformed with recombinant yeast expression vectors containing the protein or peptide coding sequences; insect cell systems infected with recombinant virus expression vectors (e.g., baculovirus) containing the protein or peptide coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the protein or peptide coding sequence; or mammalian cell systems (e.g. COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems expression vectors include but are not limited to the E. coli expression vector pUR278 (Ruther et al., 1983, EMBO J. 2:1791), in which the protein or peptide coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. PGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free reduced glutathione. The PGEX vectors are designed to include thrombin or factor Xa protease cleavage sites so that the cloned protein or peptide can be released from the GST moiety. Alternatively, the fusion protein can be left intact. In the case where the non-phosphotyrosine binding portion of the fusion protein is an enzyme, said fusion protein can be reacted with a colorometric substrate as described below. In another alternative, the non-phosphotyrosine binding portion of the fusion protein can remain uncleaved so that it may be detected by an antibody specific to it.

In an insect system, Autographa californica nuclear polyhedrosis virus (ACNPV) is used as a vector to express foreign genes. The virus grows in Spodoptera frugiperda cells. The protein or peptide coding sequence may be cloned individually into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (E.g., see Smith et al., 1983, J. Viol. 46:584; Smith, U.S. Pat. No. 4,215,051).

In mammalian host cells, a number of viral based expression systems may be utilized. In cases where an adenovirus is used as an expression vector, the protein or peptide coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins or peptides in infected hosts (e.g., See Logan & Shenk, 1984, Proc. Natl. Acad. Sci. USA 81:3655–3659). Specific initiation signals may also be required for efficient translation of inserted coding sequences. These signals include the ATG initiation codon and adjacent sequences. In cases where an protein gene, including its own initiation codon and adjacent sequences, is inserted into the appropriate expression vector, no additional translational control signals may be needed. However, in cases where only a portion of the coding sequence is inserted, exogenous translational control signals, including the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

The proteins or peptides may be produced synthetically. See, for example, Creighton, 1983, Proteins: Structures and Molecular Principles, W. H. Freeman and Co., N.Y., which is incorporated herein, by reference, in its entirety.

5.4. IMMOBILIZED PHASE

Solid phases used for the immobilization of a substrate may be prepared by coating with the anchoring molecule specific for the substrate. The anchoring molecule may be directly immobilized onto the solid phase, or, alternatively, may be indirectly immobilized to the solid phase by an antibody bound to the solid phase which is specific for the anchoring molecule. In the case where a polyclonal antibody is used as the anchoring molecule, the solid phase may first be coated with an anti-Ig that binds to the polyclonal antibody and indirectly immobilizes it to the solid phase.

The solid phase may comprise a microtiter plate, a stick, tube, disc, fiber or the like, or a microtiter plate. A preferred solid phase is a 96 well microtiter plate such as those available from Corning, Cynatech and Nunc. Particularly preferred 96 well plates are the Corning, Nunc MaxiSop and Dynatech Immulon I and IV. Ideal conditions for maximum coating with the anchoring antibody can vary with pH, ionic strength and antibody concentration. Preferred conditions will be pH 6–9.5, 0–200 mM NaCl and 1–10 μg/ml of antibody. Generally 150 μl per well is used. The anchoring molecule may be attached to the solid phase by any of a variety of methods known to those skilled in the art, including but not limited to non-covalent and covalent attachments. For example, the anchoring molecule can be applied to the solid phase in buffer for a specified period of time to allow the anchoring molecule to absorb to the solid phases, at which time the buffer is removed and blocking buffer is added. Blocking buffer may be dry milk, gelatin, bovine serum albumin or ethanolamine as a 1–5% solution in a neutral pH Tris-HCl buffer. Following the removal of the blocking buffer, the solid phase is washed and ready for use. In the case of indirect imobilization, the substrate specific antibody is added after blocking.

The anchoring molecule and the coated solid phase may be prepared ahead of time and stored until required for use in the assay.

5.5. SIGNAL-GENERATING DETECTION SYSTEMS

The detection molecules are modified by the addition of a signal-generating system to allow for detection of the detection molecules bound to phosphotyrosines in the assay system. The detection molecules may be labeled directly or can be detected using a secondary reagent that will detect the detection molecule. Such signal generating systems include, but are not limited to, enzyme-linked systems (such as horseradish peroxidase or alkaline phosphatase), radiolabels, fluorescent labels, light-emitting labels, light-absorbing labels, dyes or biotin-avidin labeling systems (e.g., See "Antibodies, A Laboratory Manual, eds. Harlow & Lane, Cold Spring Harbor Laboratory 1988, Ch. 9).

In the case of conjugated enzymes, an appropriate substrate, such as a colorimetric substrate, is added. Specific substrates used for detection include ABTS (horseradish peroxidase), DAB, AEC, BCIP/NPT (alkaline phosphatase) and BCIG (beta-galactosidase). The binding of the enzyme-conjugated anti-IgG can be then detected quantitatively by techniques well known in the art.

In a specific example described herein, an anti-rabbit IgG peroxidase conjugate is incubated with the substrate ABTS in order to facilitate detection of the bound antibody. After the reaction is stopped, the product of this reaction can be detected by determination of the O.D. at 410 nm. (Background signal measured at 630 nm is subtracted.)

5.6. EXPOSURE OF TARGET CELLS TO TEST SUBSTANCE AND PREPARATION OF CELL LYSATE

The target cells used in the present invention may express a tyrosine kinase that itself is a substrate for phosphorylation, or that phosphorylates other protein substrates upon its activation. These cells may have a tyrosine kinase that is natively expressed or they may be genetically engineered to express a specific tyrdsine kinase. The kinase may be a receptor tyrosine kinase that is responsive to an exogenous ligand. The tyrosine kinase may be a cellular kinase that is not membrane-bound, but is activated in a signal transduction pathway. The target cells of the present invention may also natively express a phosphotyrosine phosphatase (PTP), or they may be genetically engineered to express a PTP.

The test substances can be any of a variety of substances including but not limited to hormones that interact with a membrane-bound tyrosine kinase receptor, or drugs that exert their effect on the target cells through the modulation of intracellular tyrosine kinases or phosphatases. The test compounds may exert their effect through interference with ligand induced activation of a membrane-bound receptor. The test substances may be molecules that are the physiologic ligands for the receptor. They may be molecules that are not the physiologic ligands for the receptor and can be tested for an effect on the enzymatic activity of a specific receptor tyrosine kinase or phosphatase. The compounds may be drugs that modulate a receptor tyrosine kinase or phosphatase in the absence of ligand. They may be drugs that inhibit the ligand-dependent activation of a receptor tyrosine kinase or phosphatase. The present invention provides a method for the determination of the effect of a drug on specific tyrosine kinases or phosphatases by analysis of their substrates obtained from the target cell.

The target cells are grown using standard protocols for tissue culture maintenance, in which the cells are fed with appropriate medium, and incubated at the appropriate temperature with $CO_2$, if required. The substance to be tested is added to the growth medium, and the conditions of incubation with the cells are dictated by the particular assay. If a test substance is to be tested for its effect on ligand-dependent modulation of a receptor, the ligand which activates the receptor is added to the target cell in the presence of the test compound.

Following all exposures to test compounds and/or ligands, a cell lysate is prepared for analysis by immunoassay of the phosphorylated substrate. Cell lysates may be prepared by known techniques in the art in which the cell membrane is solubilized by the addition of a detergent, and the intracellular contents stabilized with the addition of buffers, protease inhibitors and phosphatase inhibitors. Detergents include but are not limited to Triton, Tween 20, X-100, NP-40, or SDS. Protease inhibitors include but are not limited to PMSF, leupeptin, EDTA and aprotinin. Phosphatase inhibitors include but are not limited to sodium orthovanadate sodium pyrophosphate and EDTA.

5.7. EXPOSURE OF SUBSTRATE IN VITRO TO TEST SUBSTANCE IN A REACTION MIXTURE

In an alternative embodiment, the effect of the test substances on the phosphorylation of the substrate of interest can be assessed in a cell-free reaction mixture. For example, to determine the effect of a test substance on kinase activity, the test substance can be incubated with the substrate of interest in a reaction mixture containing the kinase (where autophosphorylation is to be assessed, the substrate and the kinase are one and the same). The kinase reaction is then initiated by the addition of ATP and appropriate cations. The substrate is then immunoassayed for the presence of phosphotyrosine residues using an anti-phosphotyrosine detection antibody or a phosphotyrosine binding protein or peptide such as one containing an SH2 domain. The effect of the test substance on the kinase activity is reflected by the degree of phosphorylation detected in the samples treated with the test compound as compared to untreated controls.

The cell-free approach can likewise be used to determine the effects of the test substance on phosphatase activity. To this end the test compound is first incubated with a phosphorylated substrate of interest in a reaction mixture to which the phosphatase is added. The substrate is then immunoassayed for the presence of phosphotyrosine residues using an antiphosphotyrosine detection antibody or a phosphotyrosine binding protein or peptide such as one containing an SH2 domain. The effect of the test substance on the phosphatase activity is reflected by the degree of dephosphorylation detected in the samples treated with the test substance as compared to untreated controls. The phosphorylated substrate used in the assay can be obtained from cell lysates of target cells which were activated by their natural ligand. Alternatively, the substrate can be obtained from unactivated cell lysates and phosphorylated in vitro in a reaction mixture containing the kinase (where autophosphorylation is involved, the kinase and substrate of interest are one and the same), ATP and appropriate cations.

While the reaction product can be detected by any of the immunoassays described herein, a particularly rapid approach is described in the working examples, infra. Briefly, the substrate of interest can be immobilized using an anchoring antibody prior to conducting the kinase and/or phosphatase reactions in the presence of the test substances, so that all reactions are carried out on the solid phase.

6. EXAMPLE: WHOLE CELL SCREENING ASSAY

This assay assesses the potential of an exogenous test substance, applied to a cell expressing a target, to modulate the enzymatic activity of that target. In this example conditions are described for assays assessing the ability of test compounds to inhibit the kinase activity of EGFR or HER2. Those skilled in the art will recognize that such conditions can be used with other targets, such as Platelet-Derived Growth Factor receptor (PDGFR), by using a different target expressing cell and anchoring antibody. In the case of EGFR, exogenous ligand is added to stimulate the kinase activity of the receptor. In the case of HER2, kinase activity is stimulated without the addition of exogenous ligand. After exposure to the test substances, cell lysates were prepared and added to microtiter plates coated with anti-target antibody. Phosphorylation of the immobilized target was detected using anti-phosphotyrosine antisera.

6.1. MATERIALS AND REAGENTS

1. The cell line used for the EGFR assay was NIH3T3 clone 7 (EGFR/c7, Honegger, et al. Cell 51:199–209, 1987) engineered to over-express human EGFR. Growth media for these cells is DMEM (Gibco) plus 10% calf serum. The cell line used for the HER2 assay was BT 474 (ATCC HTB20) which over-expresses HER2. Growth media for these cells is RPMI (Gibco) plus 10% fetal calf serum plus GMS-G (Gibco supplement) plus glutamine.

2. The anchoring antibody used for the EGFR assay was a monoclonal antibody that recognizes the EGFR extracellular domain purchased from UBI (catalogue No. 05–101). An antibody recognizing the extracellular domain of HER2 was prepared, using techniques well know in the art, by immunizing mice with NIH3T3 cells engineered to over-express HER2. Hybridoma supernatants were screened for binding to HER2 expressing whole cells, and one clone (SUM02) was selected and grown in DMEM (GIBCO)+1% calf serum. The antibody was purified by Protein A agarose chromatography using a citric acid elution buffer, after which it was immediately neutralized. The antibody solution was dialyzed against PBS coating buffer (see below) and stored at −80° C. until used.

3. EGF was purchase from Toyobo, Co. Ltd., Japan (EGF 201), and kept as a stock solution of 16.5 µM.

4. Rabbit polyclonal antiphosphotyrosine antibody (anti-PY) was prepared according to Fendly, et al., 1990, Cancer Research 50:1550–1558.

5. Goat anti-rabbit IgG horseradish peroxidase conjugate (Tago, Burlingame, Calif., Cat.No. 4520) was used as the detection antibody.

6. TBST buffer: 50 mM Tris-HCl (pH 7.2), 150 mM NaCl, 0.1% Triton X-100.

7. Blocking buffer: TBST plus 5% milk (Carnation instant non-fat dry milk)

8. HNTG buffer: 20 mM HEPES, 150 mM NaCl, 10% glycerol, 0.2% Triton X-100, pH 7.2

9. ABTS solution: 100 mM citric acid, 250 mM Na2HPO4, 0.5 mg/ml ABTS (2,2'-azinobis(3-ethylbenzthiazlinesulfonic acid), pH 4.0.

10. Cell lysis buffer: For 10 mls–2 ml HNTG, 0.1 ml of 0.5M EDTA-HCl (pH 7.0), 0.1 ml of 0.5M Na3VO4 (kept as a 100× stock at 80 C in aliquots), 1 ml of 0.2M NaP2O7, and 7.3 mls distilled water.

11. Hydrogen peroxide: 30% solution.

12. Test substances were prepared according to Ohmichi, et al., 1993, Biochemistry 32(17):4650–4658; and Gazit, A., et al., 1991, J. Med. Chem. 34(6):1896–1907.

6.2. PROCEDURE

6.2.1. PREPARATION OF ASSAY PLATES

Microtitre plates (96 well) were coated with anchoring antibody at 0.5 µg per well in PBS (GIBCO), 150 µl final volume/well, covered with parafilm, and stored overnight at 4° C. Coated plates are good for up to 10 days when stored at 4° C. Before using, the coating buffer was removed and replaced with blocking buffer (200 µl), then incubated, shaking, at room temperature for 30 minutes. Blocking buffer was removed and the plate washed 4 times with TBST buffer.

6.2.2. SEEDING CELLS

Cells were grown in tissue culture dishes until 80–90% confluence then collected by trypsinization (0.25% trypsin-EDTA (Gibco)) The reaction was stopped with the addition of 10% FCS. The cells were suspended in fresh medium, and centrifuged once at 1500 rpm, room temperature, for 5 minutes. The cells were resuspended in fresh medium and transferred to 96 well tissue culture plates (Corning, 25806-96) (10,000 cells/well for EGFR/c7 starved at 0.5% FES for 40–48 hrs; 25,000 cells/well for BT474) at 100 μl/well. The plates were incubated at 37° C. in 5% $CO_2$, overnight.

6.2.3. ASSAY PROCEDURE

Media in the wells was replaced by serum free growth medium (DMEM or RPMI), 90 μl per well. Serial dilutions of test compound stocks (10 mg/ml in DMSO) were diluted 1:10 into growth media (DMEM or RPMI) and 10 Al added per well for a final concentration range of 100 μM to 1 nM. (In a primary screen, 10 mg/ml test compound stock (in DMSO) is diluted 1:10 into serum free growth medium for final concentrations of 1:200 for the test substance and 0.5% for DMSO in the well.) Control wells received DMSO and serum free medium only. The cells were incubated for 1 hour at 37 C, 5% $CO_2$.

For the EGFR assay, EGF was diluted in DMEM such that upon transfer of 10 μl of dilute EGF (1:12 dilution, a 25 nM concentration is attained in the microtitre well. After the 1 hour incubation with the test drug, 10 μl of EGF was added per well. Control wells received DMEM alone. The plate was incubated, shaking, at room temperature an additional 5 minutes.

For both assays, after incubation all solution was removed and the wells washed twice with PBS. Cell lysis buffer (100 μl) was added to each well, then the plate was left on ice for 5-10 minutes. The assay plates were emptied by removing the blocking buffer and washing with TBST.

Cells were scraped from the microtiter wells and homogenized using a pipette tip and repeated aspirating and dispensing. The cell lysate was transferred to the assay plate wells, and the target substrate was allowed to bind for 1 hour at room temperature, shaking. The lysate was removed, and the plate washed 4 times with TBST.

Phosphotyrosine was detected by the addition of anti-PY (100 μl per well, diluted 1:3,000 with TBST), then incubated, shaking, at room temperature for 30 minutes. The anti-PY solution was removed, and the plate washed 4 times with TBST. Detecting antibody was added (100 μl per well, diluted 1:3,000 with TBST), and the plate was incubated for 30 minutes at room temperature, shaking. The detecting antibody solution was removed, the plates were washed with TBST (4×) and fresh ABTS/$H_2O_2$ was added (100 μl per well) to start color development. (ABTS/$H_2O_2$ is prepared with 1.2 μl $H_2O_2$ to 10 ml BTS.) Color was allowed to develop for 20 minutes at room temperature. Color development may be stopped by the optional step of adding 50 μl 5N $H_2SO_4$. Optical density is measured at 410 nM (Dynatec MR5000).

6.3. RESULTS

Example results are shown in Table I (EGFR) and Table II (HER2).

TABLE I

| EFFECT OP TEST SUBSTANCES ON KINASE ACTIVITY OP EGF-R ACTIVATED BY EGFR | |
|---|---|
| Test Substance | IC50 (μM) |
| 42 | >50 |
| 957 | 43.6 |
| 48 | >100 |

TABLE II

| EFFECT OF TEST SUBSTANCES ON HER2 | |
|---|---|
| Test Substance | IC50 (μM) |
| 42 | >50 |
| 48 | 41.5 |
| 56 | 30.1 |

7. EXAMPLE: CELL-FREE SCREENING ASSAY FOR KINASE ACTIVITY

This assay provides a method for measuring the effects of test substances on the kinase activity of specific targets in a cell-free system. The target substrate is isolated from cell lysates by immobilization in microtiter plate wells coated with anti-substrate antibody. Following addition of the test substance, ATP and a bivalent cation are added to the wells to initiate the kinase-reaction. Concentrations of ATP can be varied to assess whether a test compound competes for ATP or substrate interaction. The concentration of ATP should be <3 μM for assessing high sensitivity in the kinase reaction. A concentration of 10–50 μM ATP, is preferred for assessing inhibition of ATP interaction, and most preferably 50 μM. At this ATP concentration the assay will identify inhibitors that do not compete well with ATP. Phosphorylation of tyrosine residues on the immobilized target is then detected using antiphosphotyrosine antiserum.

7.1. MATERIALS AND REAGENTS

The materials and reagents used are described in Section 6.1 with the exception that the cells used to prepare the cell lysate were another EGFR over-expressing human epidermoid carcinoma cell line, A431 (ATCC CRL 1555). Test substances were obtained from LC Service Corp (Woburn, Mass.).

7.2. PROCEDURE

7.2.1. PREPARATION OF ASSAY PLATES

Preparation of the assay plates was performed as described in Section 6.2.1.

7.2.2. PREPARATION OF CELL LYSATE

Cells (A431) were grown to 80–90% confluency in DMEM (Gibco) plus 10% calf serum then washed twice with PBS. HNTG was added and the dish place on ice for five minutes. Cells were scraped from the plate and homogenized as described in Section 6.2.3, transferred to a test tube, and cleared of cell debris by centrifugation (10,000×g, 10 minutes, 4° C.). The cleared lysate can be stored at −80 C until used.

7.2.3. ASSAY PROCEDURE

Seven μg of cell lysate was added to each well of a prepared assay plate plus PBS to make a final volume of 150

μl. The plate was incubated for 30 minutes, shaking, at room temperature, then washed five times with TBST. Serial dilutions of test compound stocks (10 mg/ml in DMSO) were diluted 1:20 into 5% DMSO in PBS for a final concentration range of 150 μM to 1 nM, then 135 μl was added per well. The plate was incubated for 30 minutes, shaking, at room temperature.

The kinase reaction was initiated by the addition of 15 μl of ATP/Mn mix (in 50 mM $MnCL_2$, final concentration of ATP 1 μM, 3 μM or 10 μM) for a total volume of 150 μl. The plate was incubated for 5 minutes at room temperature, shaking, then washed 5 times with TBST. The amount of phosphorylation present was measured as described in Section 6.2.3.

7.3. RESULTS

TABLE III

EFFECT OF TEST SUBSTANCES ON EGF-R KINASE ACTIVITY A CELL FREE SYSTEM

| Test Substance | ATP Conc. (μm) | IC50 (μM) |
| --- | --- | --- |
| Genestein | 10 | 150 |
|  | 3 | 10 |
|  | 1 | 6 |
| Lavendustin A | 10 | 55 |
|  | 3 | 0.1 |
|  | 1 | 0.08 |
| Staurosporin | 10 | 100 |
|  | 3 | 10 |
|  | 1 | 8 |
| Herbimycin A | 1 | >100 |

8. EXAMPLE: CELL FREE PHOSPHATASE ASSAY

This assay provides a method for measuring the effects of test substances on the phosphatase activity of PTP 1B as measured by dephosphorylation of EGFR. The assay protocol used is substantially the same as that described in Section 7.

8.1. MATERIALS AND REAGENTS

The materials and reagents used are substantially the same as those described in Section 7.1 with the following additions.

1. TBS: 50 mM Tris, pH 7.2, 150 mM Nacl
2. PTP 1B: the protein was produced in bacterial cells (strain B121) using a pET plasmid with a T7 promoter, Tonks, et al. Methods in Enzymology 201:427–443, 1991.
3. phosphatase buffer: 100 mM Tris, pH 7.2, 5% DMSO, 1.5 mM NaPyrophsophate.

8.2. PROCEDURE

8.2.1. PREPARATION OF ASSAY PLATES

Preparation of the assay plates was performed as described in Section 7.2.1.

8.2.2. PREPARATION OF CELL LYSATE

Preparation of the cell lysate was performed as described in Section 7.2.1.

8.2.3. ASSAY PROCEDURE

The assay procedure used was substantially the same as that described in Section 8.2.3 with the following changes.

After binding of the EGFR substrate to the microtiter wells and washing 5 times with distilled water and once with TBST, a kinase reaction was initiated by adding 135 μl of TBS per well, then 15 μl of 0.003 mM ATP in 50 mM $MnCl2$, for a final concentration of 3 μM ATP and 5mM MnCl2. The reaction was allowed to proceed for 5 minutes, shaking, then stopped with the addition of 16.5 μl of 200 mM EDTA, pH 8.0, shaking continuously during this addition. The plate was left shaking for an additional minute then washed 5 times with distilled water and once with TBST.

Test compounds were diluted 1:100 in phosphatase buffer, and aliquots of 140 μl were added to each well. Control wells received phosphatase buffer alone.

The phosphatase reaction was initiated by the addition of PTP 1B diluted in 100 mM Tris, pH 7.2 (10 μl (20 ng) per well). The plate was incubated for 15 minutes, shaking, then washed 5 times with distilled water and once with TBST. The amount of phosphotyrosine remaining is measured as described in Section 6.2.3.

8.3. RESULTS

The results shown in Table IV below demonstrate that test compounds can be assessed quantitatively for their ability to inhibit phosphatase activity in a cell free system.

TABLE IV

EFFECT OF TEST SUBSTANCES ON PHOSPHATASE 1B ACTIVITY ON THE EGFR IN VITRO

| Test Substance | IC50 (μM) |
| --- | --- |
| NaVanadate | 30 |

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An assay for screening test substances for the ability to modulate activity of a specific protein tyrosine kinase involved in signal transduction, comprising:

(a) contacting (i) a lysate of a target cell which was exposed to the test substance with (ii) an anchoring molecule specific for a protein substrate which is phosphorylated as a result of signal transduction in the target cell, under conditions and for a time sufficient to allow binding of the protein substrate to the anchoring molecule thereby rendering the protein substrate immobilized; and (b) detecting phosphotyrosine residues on any protein substrate bound to the anchoring molecule, in which differences in the detection of phosphotyrosine residues on the immobilized protein substrate derived from lysates of the target cells which were exposed to the test substance as compared to that of immobilized protein substrate derived from control target cells which were not exposed to the test substance, indicate that the test substance modulates the activity of the tryrosine kinase involved in a signal transduction.

2. The assay of claim 1 in which the anchoring molecule is a antibody.

3. The assay of claim 1 in which the phosphotyrosine residue is detected using an antibody specific for phosphotyrosine.

4. The assay of claim 3 in which the antibody specific for phosphotyrosine is a monoclonal antibody.

5. The assay of claim 3 in which the antibody specific for phosphotyrosine is labeled.

6. The assay of claim 5 in which the label is selected from the group consisting of a radiolabel, a fluorescent label, a luminescent label and an enzymatic label.

7. The assay of claim 3 in which the antibody specific for phosphotyrosine is indirectly labeled.

8. The assay of claim 7 in which the antibody specific for phosphotyrosine is indirectly labeled with a label selected from the group consisting of a radiolabeled anti-immunoglobulin, a fluorescently labeled anti-immunoglobulin, a luminescently labeled anti-immunoglobulin, and an enzymatically labeled anti-immunoglobulin.

9. The assay of claim 2 in which the antibody is bound to a microtiter plate.

10. An assay for screening test substances for the ability to modulate activity of a specific protein tyrosine phosphatase involved in signal transduction, comprising:

(a) contacting (i) a lysate of a target cell which was exposed to the test substance with (ii) an immobilized antibody specific for a protein substrate which is dephosphorylated as a result of signal transduction in the target cell, under conditions and for a time sufficient to allow binding of the protein substrate to the immobilized antibody thereby rendering the protein substrate immobilized; and (b) detecting phosphotyrosine residues on any protein substrate bound to the immobilized antibody, in which differences in the detection of phosphotyrosine residues on the immobilized protein substrate derived from lysates of the target cells which were exposed to the test substance as compared to that of immobilized protein substrate derived from control target cells which were not exposed to the test substance, indicate that the test substance modulates the activity of the tyrosine phosphatase involved in a signal transduction.

11. The assay of claim 10 in which the anchoring molecule is a antibody.

12. The assay of claim 10 in which the phosphotyrosine residue is detected using an antibody specific for phosphotyrosine.

13. The assay of claim 12 in which the antibody specific for phosphotyrosine is a monoclonal antibody.

14. The assay of claim 12 in which the antibody specific for phosphotyrosine is labeled.

15. The assay of claim 14 in which the label is selected from the group consisting of a radiolabel, a fluorescent label, a luminescent label and an enzymatic label.

16. The assay of claim 12 in which the antibody specific for phosphotyrosine is indirectly labeled.

17. The assay of claim 16 in which the antibody specific for phosphotyrosine is indirectly labeled with a label selected from the group consisting of a radiolabeled anti-immunoglobulin, a fluorescently labeled anti-immunoglobulin, a luminescently labeled anti-immunoglobulin, and an enzymatically labeled anti-immunoglobulin.

18. The assay of claim 11 in which the antibody is bound to a microtiter plate.

19. The assay of claim 1 or claim 10, wherein the test substance is a therapeutic compound that modulates kinase or phosphatase activity and the assay is used to determine whether said target cell will respond to said therapeutic compound.

20. The assay of claim 19, in which the target cell is a cell in which a pathological process correlating with a disease state is derived from a patient exhibiting said disease state, thereby determining whether said target cell will respond to said therapeutic compound.

21. The assay of claim 20, in which the disease state is selected from the group consisting of neoplasia, cancer and diabetes.

22. An assay for screening test substances for the ability to modulate the level of phosphotyrosine on a specific protein substrate involved in signal transduction, comprising:

(a) contacting a lysate of a target cell, after the target cell was exposed to a test substance, with an immobilized antibody specific for a protein substrate which is phosphorylated or dephosphorylated as a result of signal transduction in the target cell, under conditions and for a time sufficient to allow binding of the protein substrate to the immobilized antibody thereby rendering the protein substrate immobilized; and (b) detecting phosphotyrosine residues on any protein substrate bound to the immobilized antibody, in which differences in the detection of phosphotyrosine residues on the immobilized protein substrate derived from lysates of the target cells which were exposed to the test substance as compared to that of immobilized protein substrate derived from control target cells which were not exposed to the test substance, indicate that the test substance modulates the phosphotyrosine lever of the protein substrate.

* * * * *